United States Patent [19]

Marsik

[11] Patent Number: 4,788,984

[45] Date of Patent: Dec. 6, 1988

[54] METHOD AND KIT FOR USE IN CONCEIVING A CHILD OF A DESIRED GENDER

[75] Inventor: Robert W. Marsik, Englewood, Colo.

[73] Assignee: ProCare Industries Ltd., Englewood, Colo.

[21] Appl. No.: 9,206

[22] Filed: Jan. 30, 1987

[51] Int. Cl.$^4$ ............................................. A61B 10/00
[52] U.S. Cl. ..................................... 128/738; 436/65
[58] Field of Search ............. 128/630, 736, 738, 759; 604/55; 73/54, 60; 235/88 RC; 436/65; 40/124, 124.2, 124.4, 312, 380; 206/569, 570

[56] References Cited

U.S. PATENT DOCUMENTS

| | | | |
|---|---|---|---|
| 927,107 | 7/1909 | Bryant | 40/380 |
| 1,487,014 | 3/1924 | Davis | 206/570 |
| 3,935,944 | 2/1976 | Wilson et al. | 206/569 |
| 4,036,212 | 7/1977 | Karahn | 128/738 |
| 4,122,947 | 10/1978 | Falla | 206/569 |
| 4,151,831 | 5/1979 | Lester | 128/736 |
| 4,339,434 | 7/1982 | Ericsson | 128/1 R |
| 4,358,288 | 11/1982 | Goldman | 436/65 |
| 4,465,077 | 8/1984 | Schneider | 128/736 |
| 4,508,829 | 4/1985 | Sulitzeanu | 436/65 |
| 4,670,401 | 6/1987 | Cutler et al. | 436/65 |

OTHER PUBLICATIONS

Hazel Phillips, *Girl or Boy?*, Your Chance to Choose, Thorson's Publisher's, Ltd., Great Britain, 1985.
Mercedes Arzu Wilson, *Love and Fertility*, Family of the Americas Foundation, Inc., (1986).
Elizabeth Whelan, *Boy or Girl?*, The Bobbs-Merrill Company, Inc.
Franciszek Benendo, "The Problem of Sex Determination in the Light of Personal Observation," *Polish Endocrinolgy*, vol. 21, No. 3, (1970).
B. Seguy, "Determination Et Selection Volontaires du Sexe," *La Novelle Pressee Medicale*, Feb. 21, 1976.
B. Seguy, "Les Methodes de Selection Naturelle et Volontaire des Sexes," *J. Gyn. Obst. Biol. Repr.*, 1975, pp. 145-149.
Evelyn Billings, *The Billings Method*, pp. 70-71, Ballantine Press.

*Primary Examiner*—Max Hindenburg
*Attorney, Agent, or Firm*—Sheridan, Ross & McIntosh

[57] ABSTRACT

A method and a kit are provided for use in conceiving a child of a desired gender. The kit contains all information, instructions, and apparatus that is necessary for predicting ovulation time and for determining time periods which define that time during which intercourse results in an improved probability of conceiving a child of the desired gender. The kit also contains information regarding the effects of the sperm placement location and timing of orgasm on gender selection. The kit includes information and instructions relating to practicing the method. A mucus chart is provided for monitoring the state of mucus of the woman attempting to conceive a child. Tissues are also part of the kit and are used in obtaining samples of the mucus. The kit further includes temperature sensors and a temperature chart for keeping track of the basal body temperature of the woman. These temperature-related products assist the user in confirming the prediction of ovulation. For ease of access and selection, the kit products are contained in individual packets of various sizes. Each of the packets is preferably housed in a convenient and desirably shaped container.

5 Claims, 9 Drawing Sheets

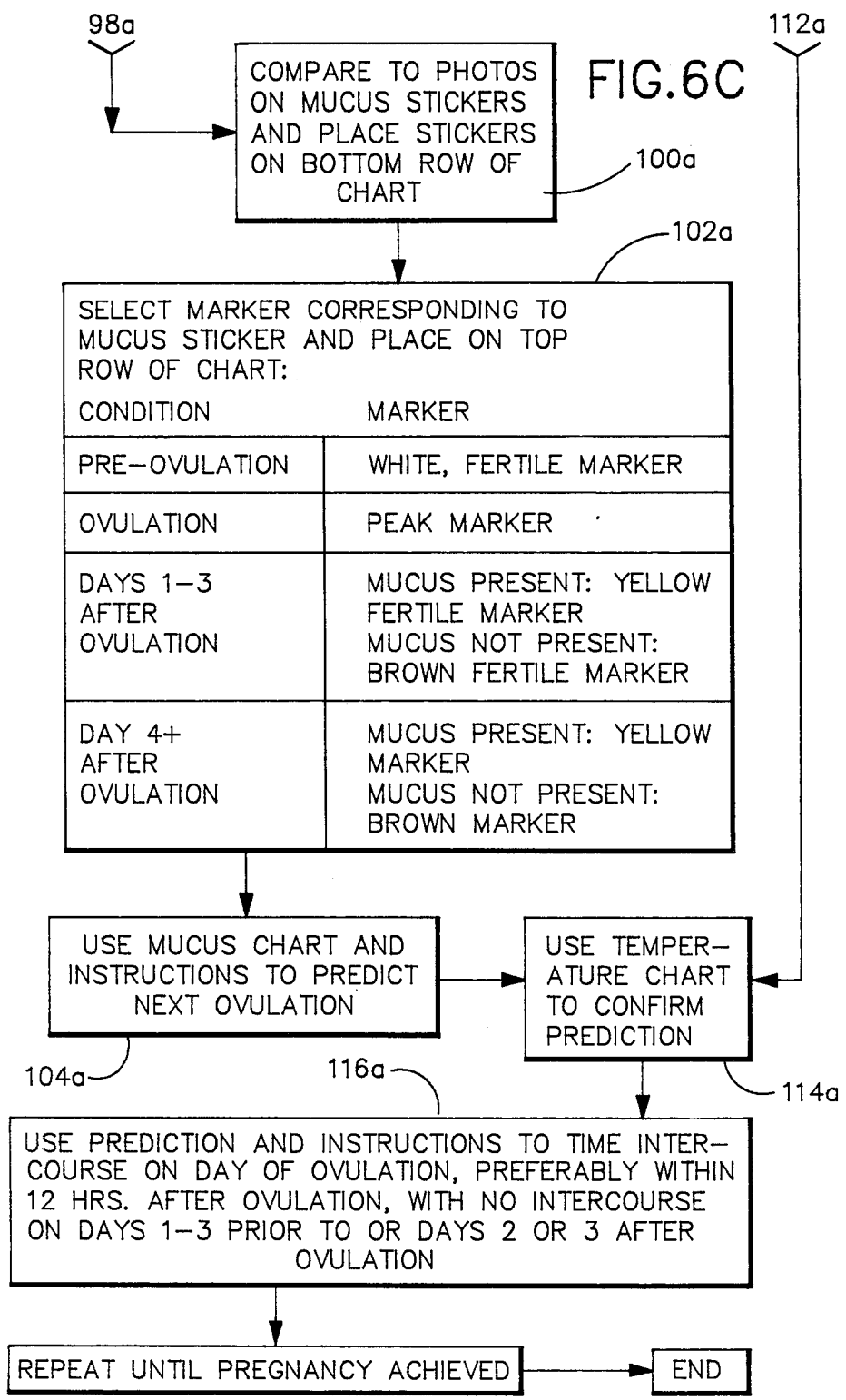

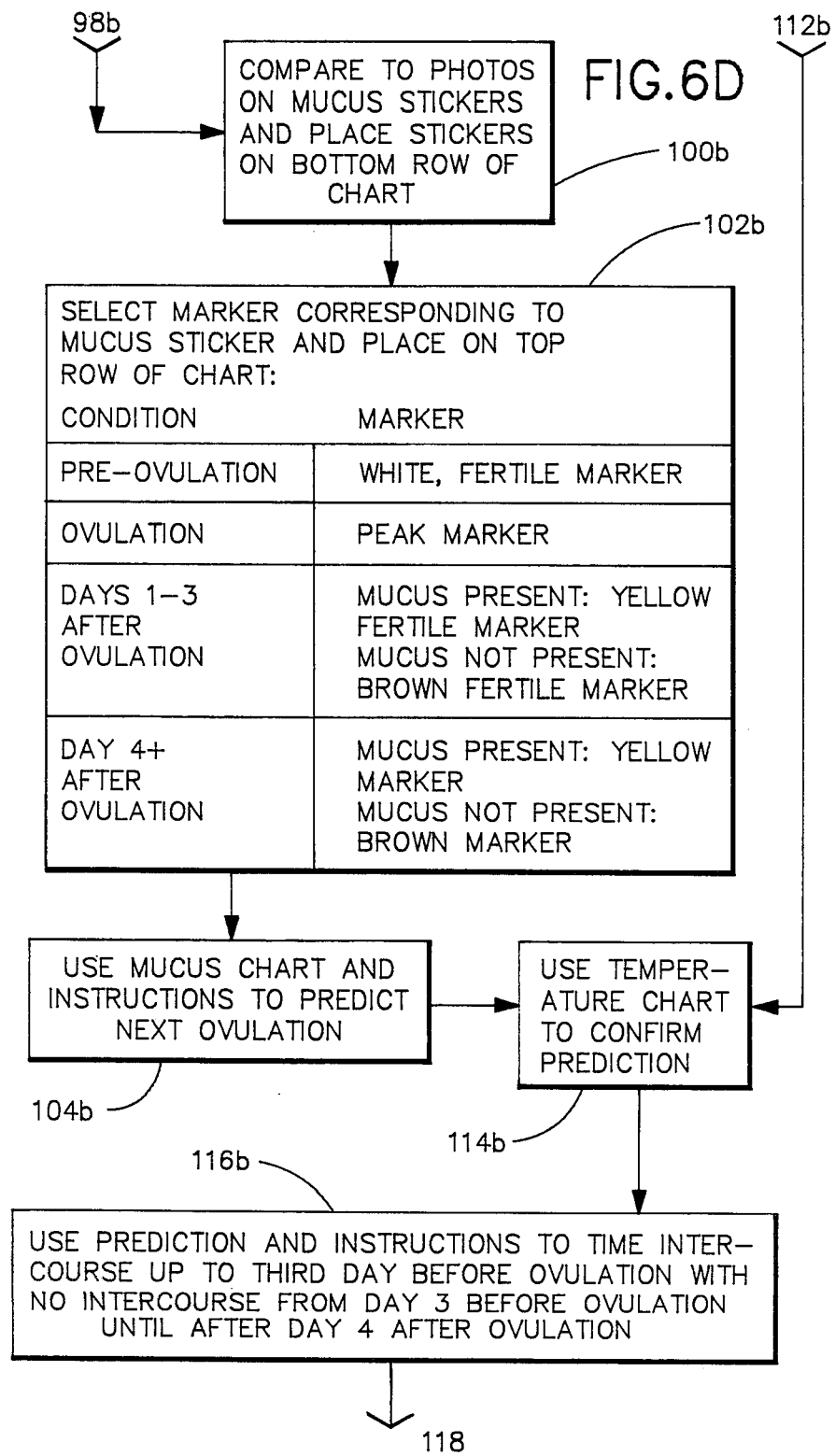

METHOD AND KIT FOR USE IN CONCEIVING A CHILD OF A DESIRED GENDER

FIELD OF THE INVENTION

The present invention relates to a method and a kit for use in attempting to conceive a child and particularly to a method and kit for use in predicting a period of time during which intercourse is likely to result in conception of a child of a desired gender.

BACKGROUND INFORMATION

It is known that the live birth male sex ratio, while differing among cultures, in the United States is about 53 percent (i.e. 53 percent male, 47 percent female). In many instances, a couple may prefer to conceive a child of one or the other gender. Often this preference is for traditional or personal reasons. Further, a couple with children of one sex may wish to experience parenting of both sexes. Also, a number of genetic disorders or diseases are known to be sex-linked (e.g. hemophilia) and couples who have this genetic disposition may desire to conceive a child of the gender opposite the sex-linked gender to avoid or reduce the likelihood of the disorder or disease.

Theories and methods associated with altering the probability of conception of a child of a selected gender have been discussed. In Hazel Phillips, *Girl or Boy Your Chance To Choose* (Thorson's Publishers, Ltd., Great Britain), the effects of intercourse timing and position are noted in attempting to conceive a child of a selected gender. In Mercedes Arzu Wilson, *Love and Fertility*, Family Of The Americas Foundation, Inc. (1986), although a method of achieving pregnancy using the mucus method is noted, there is no discussion concerning child gender selection.

A chemical-related test for use in child gender selection has been developed and involves the separation of sperm. The desired, separated sperm are then artificially inseminated for the purpose of attempting to conceive a child of a selected gender. This technique is accomplished in a hospital or laboratory-like environment. It also requires highly skilled personnel and is relatively expensive.

Because of the relative complexity and expense of this prior art technique, it would be advantageous to provide a method that could be employed in privacy at home without the need for highly technical skills and equipment, and which does not include numerous and complicated steps. In that regard, it would be desirable to incorporate in a single package or kit all the information and materials that would be needed in the home in attempting to conceive a child of a selected gender. Although information for use in practicing the mucus method and/or temperature method of ovulation prediction is available, no single source or package of information and apparatus has been devised for use in attempting to conceive a child of a selected gender, preferably, in the privacy of one's home.

SUMMARY OF THE INVENTION

In accordance with the foregoing objectives, the present invention provides in a single package or source all of the information and apparatus to be used in connection with attempting to conceive a child of a chosen gender. The method includes providing a single kit having a number of related products for use in implementing the method steps. The products include instructional literature explaining the method and apparatus for predicting ovulation, timing of intercourse, and other aspects of gender selection. The apparatus for predicting the ovulation body function includes apparatus directed to the mucus method of ovulation prediction. Such apparatus includes mucus charts for monitoring the state of the mucus of a woman and any changing pattern thereof, as well as tissues for collecting mucus. The charting also provides recordkeeping of sexual activity. In addition, apparatus for the basal temperature method of ovulation prediction is provided. This apparatus is intended to be used to confirm the results of the ovulation prediction obtained using the mucus method steps. Such apparatus includes temperature charts for monitoring body temperature of the woman attempting to conceive a child and devices for sensing temperature prior to normal physical activity occurring. The method further includes using the mucus method and apparatus to predict ovulation, while using the basal body temperature method and apparatus to verify the accuracy of such prediction. More particularly, the mucus ovulation prediction method involves obtaining mucus of the woman using the tissues and monitoring the state of mucus using the mucus chart. The basal temperature of the woman is obtained using the temperature sensing devices and such temperatures are recorded using the temperature charts. The method further involves attempting to conceive a child by having intercourse within a predetermined period of time using information previously provided on the mucus chart and the temperature chart.

The single kit preferably also includes a container for housing the kit products. The container is shaped to permit ready access by the user to the kit products. Also facilitating selection or access to the products is the individual packaging of the kit products. Specifically, the kit is provided with four individual packets, with each packet being of a different size to permit ready viewing of the separate packets so that the desired packet can be more easily selected from the container.

In view of the foregoing summary, a number of important features of the present invention are immediately discerned. A child gender selection kit is provided for use in the privacy of one's home. The kit provides in a single package all of the information and materials that are necessary in practicing the method of the present invention. No complex techniques or specialized skill is required to utilize the kit products or practice the method.

Additional advantages of the present invention will become readily apparent from the following discussion, particularly when taken in conjunction with the accompanying drawings.

DETAILED DESCRIPTION

The present invention relates to a method and a kit for use in attempting to conceive a child of a desired gender. The kit includes information, instructions and all materials necessary to achieve an improved probability of conceiving a child of the desired gender.

Figure 1:
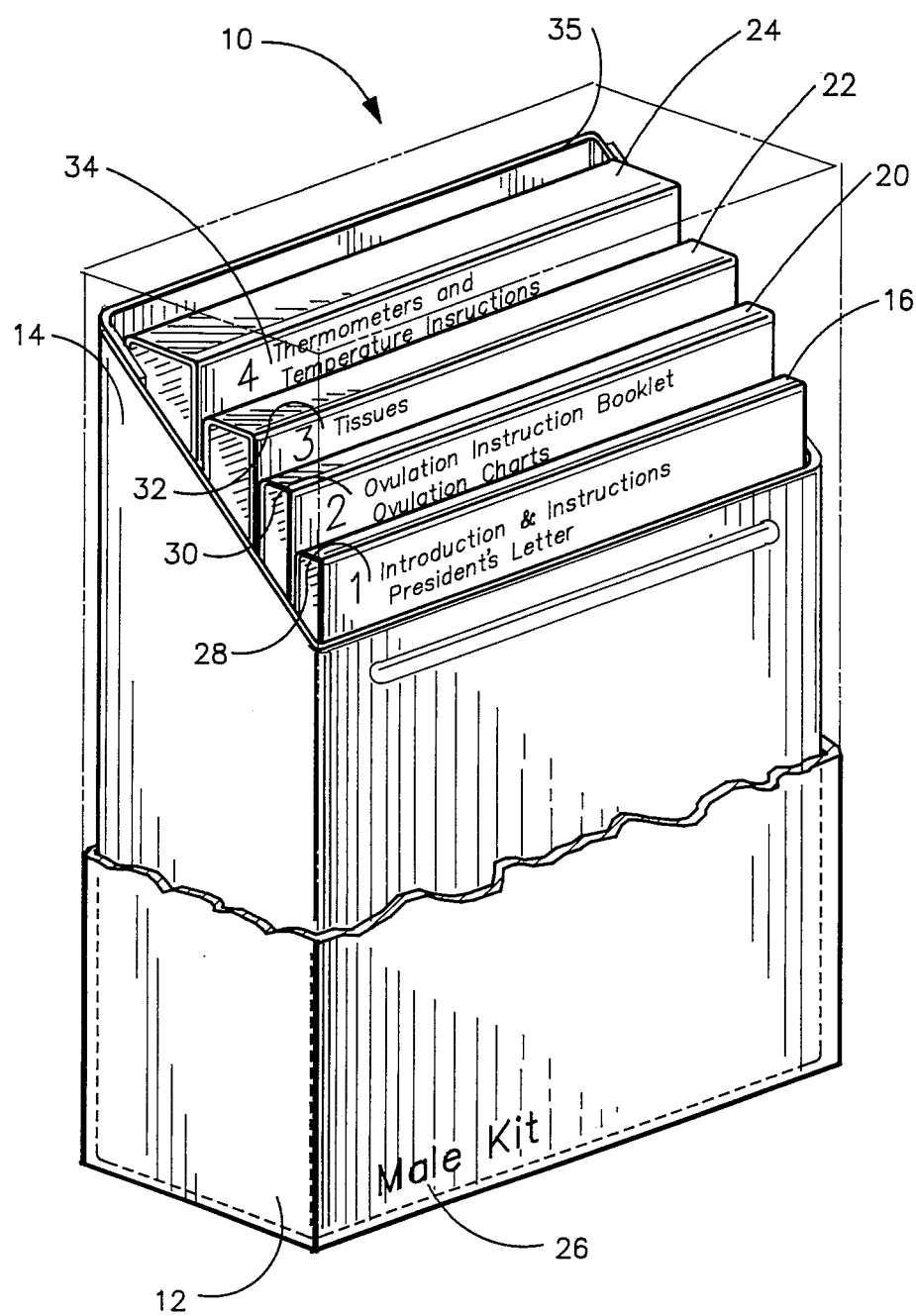
FIG. 1 is a perspective view of a kit for use in conceiving a child of a desired gender with portions broken away to show four packets therein.

As depicted in FIG. 1, the kit 10 comprises a box or package 12 housing an open-ended container or caddy 14 and four packets 16, 20, 22, 24. The packets 16–24 are formed of any convenient material, such as folded and pasted cardboard and are preferably of different sizes, e.g., the first packet 16 has a height less than that of the second packet 20 which has a height less than that of the third packet 22 which has a height less than that of the fourth packet 24. The box 12 can be in any convenient form such as folded and pasted cardboard and preferably contains indicia 26 identifying the kit as pertinent to male child selection or female child selection. Although FIG. 1 depicts a kit for use in attempting to conceive a male child, the kit for use in attempting to conceive a female child is substantially identical except that the instructions contained therein are different, consistent with the differing methods for male and female child conception, as discussed below.

The caddy 14 is preferably made of a cardboard material, or other kinds of sturdy material and is configured to hold the packets 16–24 in a position to permit viewing of the packet indicia 28–34 and to permit easy access to any one of the packets 16–24 as needed to practice the method, described below. As seen in FIG. 1, the indicia 28–34 identifies each of the packets 16–24, respectively. By providing a caddy 14 which is separable from and removable from the box 12 the contents of the kit 10 can be contained in a single unit. As depicted, the caddy 14 is preferably formed with a top opening 35 which is inclined with respect to a horizontal surface. This configuration of the caddy 14 cooperates with the different heights of the packets 16–24 so that each packet is readily accessible and each of the indicia of the packets 28–34 is readily visible.

Figure 2:
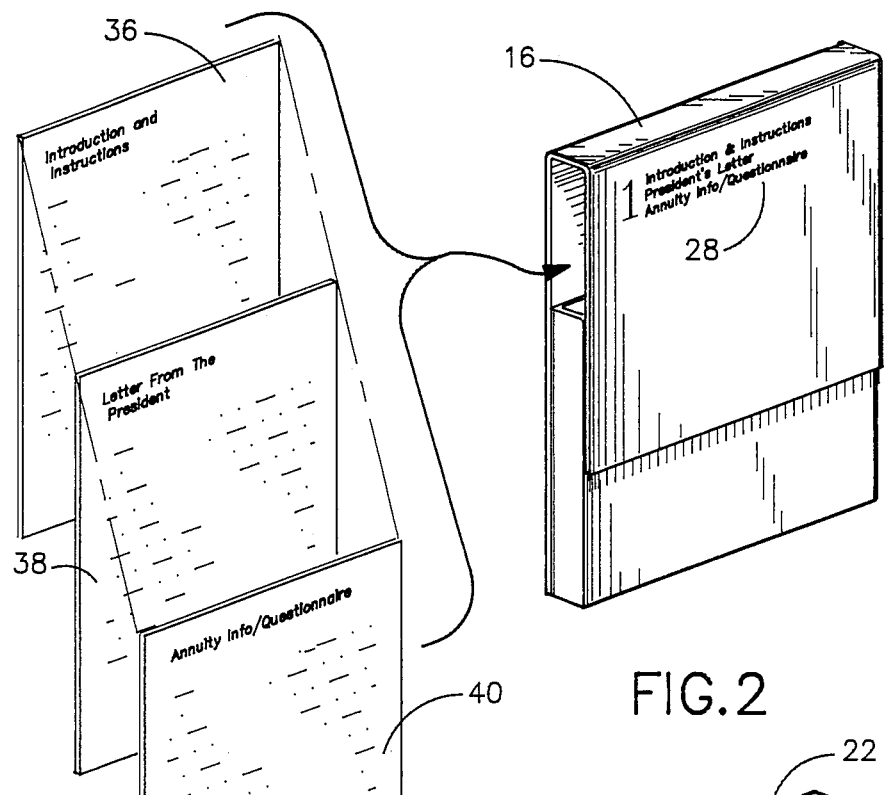
FIG. 2 is a perspective view of the first packet with the contents thereof shown in an exploded view.

As best seen in FIG. 2, the first packet 16 contains information and instructions in the form of printed material 36. The information and instructions 36 explain the contents of the kit 10, the use of each of the products contained in the kit 10 and the manner in which the method of the present invention is practiced in order to achieve improved probability of conceiving a child of a desired gender. Other informational materials are, preferably, included in the first packet 16 such as an introduction and letter from the manufacturer or distributor 38, a questionnaire and information on other aspects of the product such as an annuity program 40, which is useful in monitoring the degree of success of the method and kit.

Figure 3:
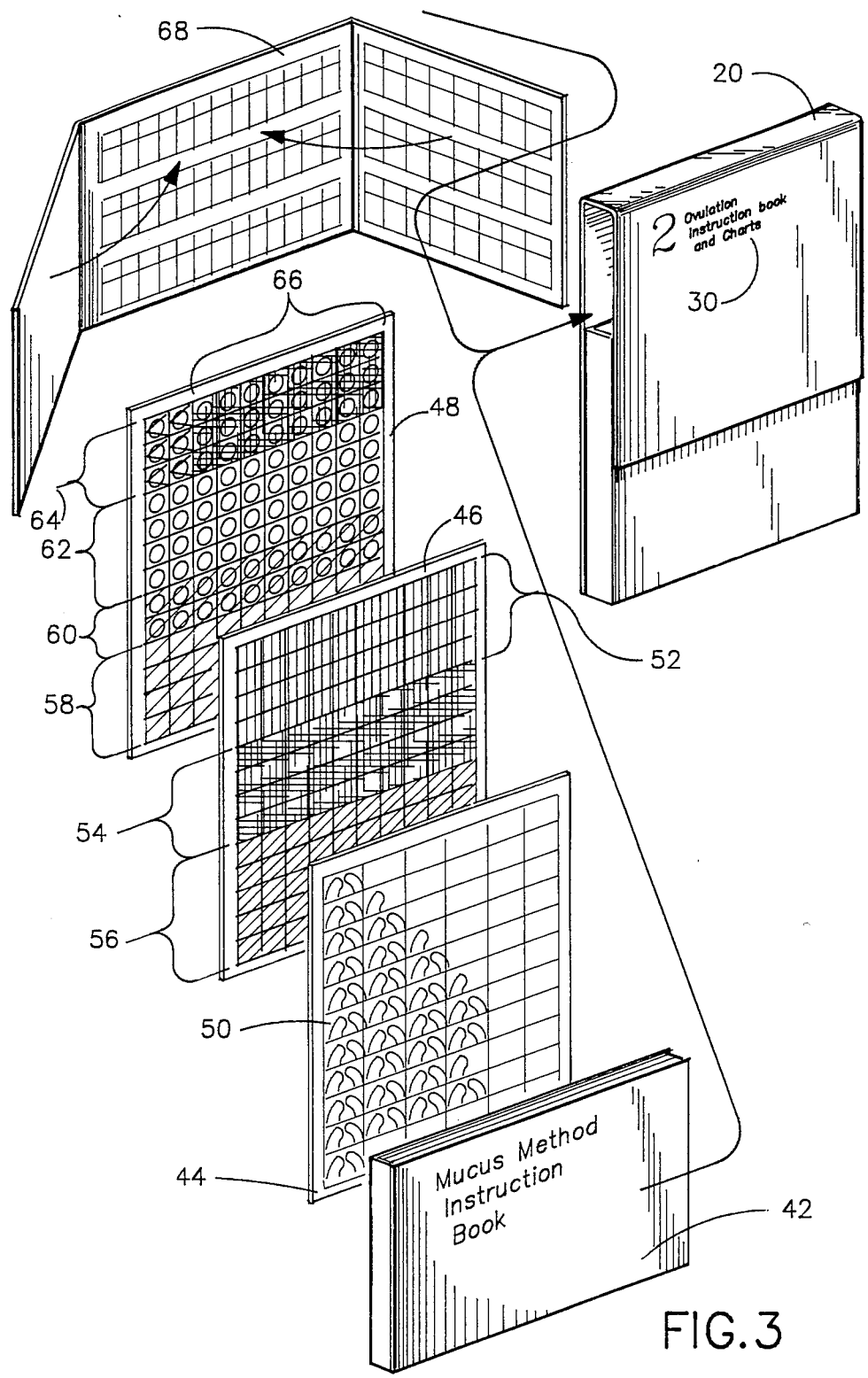
FIG. 3 is a perspective view of the second packet with the contents thereof shown in an exploded view.

As best seen in FIG. 3, the second packet 20 contains a number of materials for use in connection with the mucus technique of ovulation prediction. An instruction book 42 provides information and instructions explaining the use of the other contents of the second packet 20 and explaining the method of using the woman's mucus to predict ovulation time. A number of sheets bearing gummed stickers 44, 46, 48 are also included. The first sheet 44 bears a number (e.g. 78) of stickers each having a photograph depicting mucus state. The second sheet 46 bears a number (e.g. 40) of red stickers 52, a number (e.g. 40) of yellow stickers 54 and a number (e.g. 50) of plain brown stickers 56. The third sheet 48 bears a number (e.g. 40) of plain brown stickers 58, a number (e.g. 20) of brown stickers bearing fertility indicia, such as a drawing of a child's face 60, a number (e.g. 40) of white stickers having fertility indicia 62, a number (e.g. 4) of white stickers having both fertility indicia and peak indicia (e.g. an upside-down "V") 64 and a number (e.g. 24) of yellow stickers bearing fertility indicia 66. Also included in the second packet 20 is a chart booklet 68 having a number (e.g. 3) of charts, each chart having a space for noting the date, top and bottom rows each having a number (e.g. 35) of spaces, the bottom row spaces being of a size for entering mucus stickers and the top row spaces being of a size for entering other stickers. The chart also has, positioned next to the spaces for each day, day and night indicia (e.g. sun and moon symbols). Each of these chart-related materials is available from the Family of the America's Foundation, Inc. of Mandeville, La.

Figure 4:
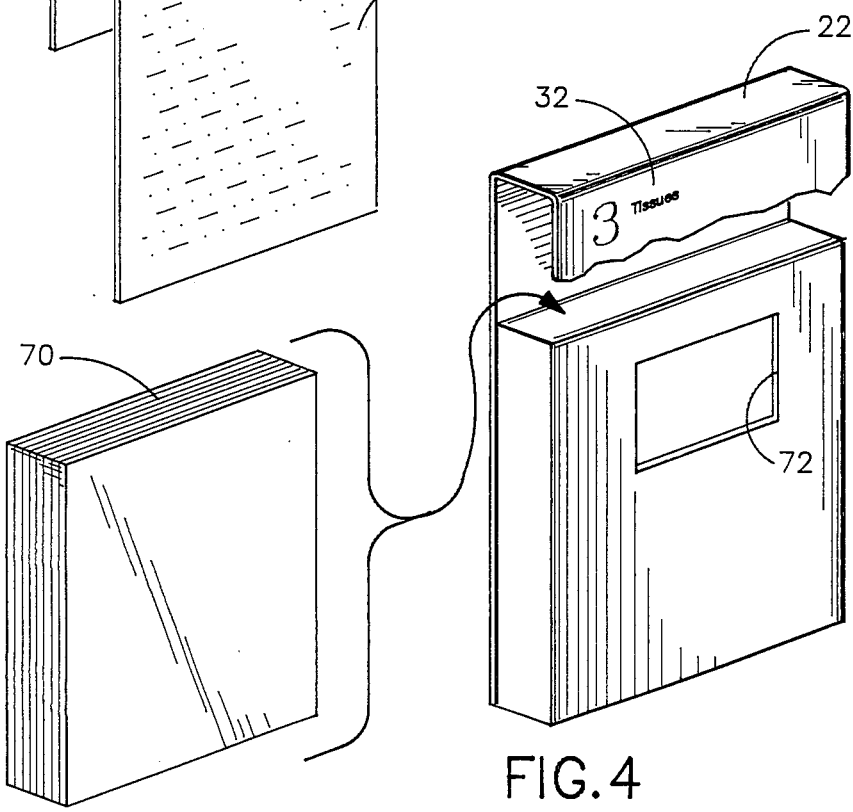
FIG. 4 is a perspective view of the third packet with the contents thereof shown in an exploded view.

As best seen in FIG. 4, the third packet 22 contains a number of tissues 70. The tissues can be of any size convenient for mucus collection such as about 8 inches by about 4½ inches, preferably folded in half. The tissues can be formed of any suitable soft material. The third packet 22 is preferably formed with a window 72 in one face thereof through which the tissues 70 can be removed.

Figure 5:
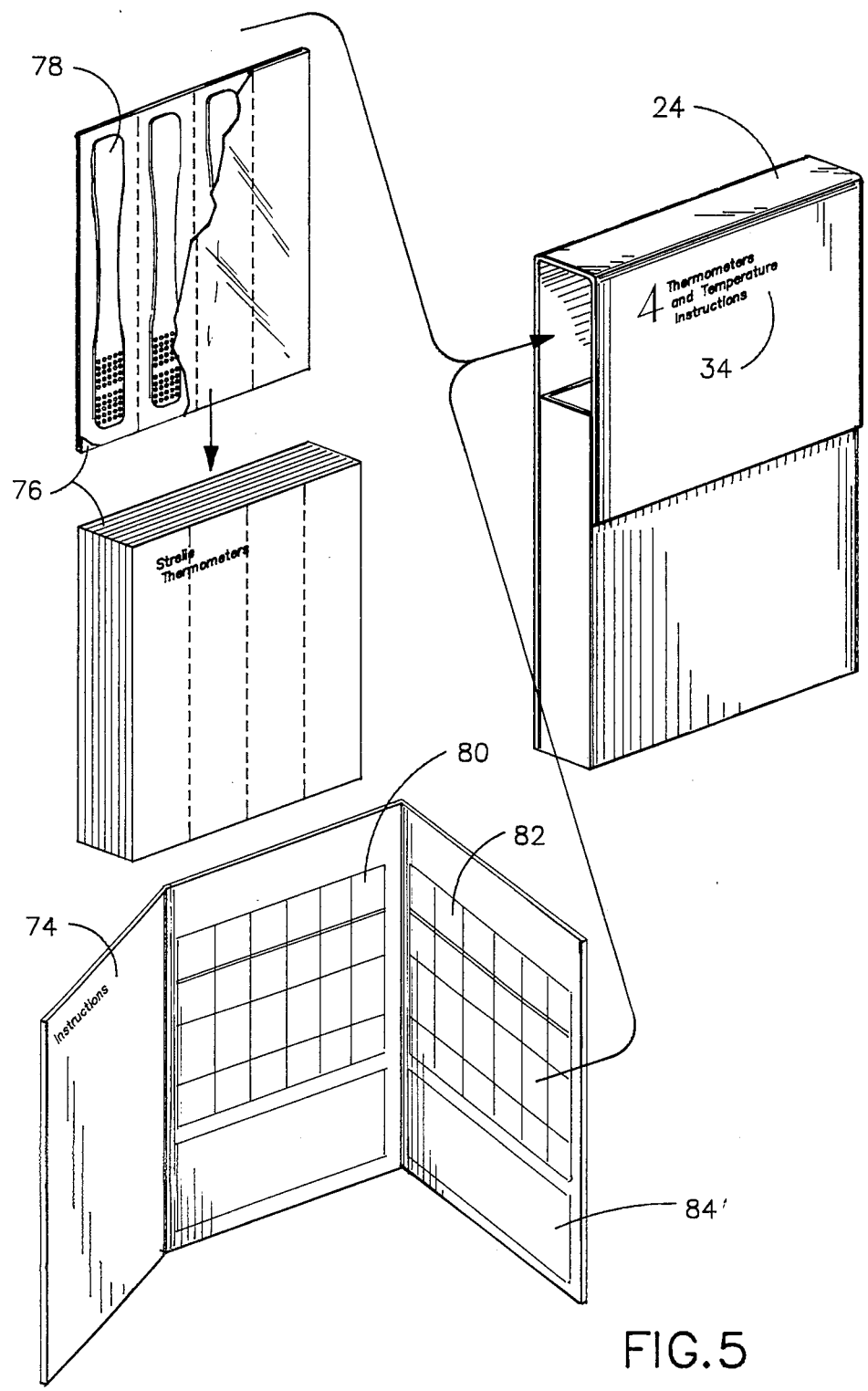
FIG. 5 is a perspective view of the fourth packet with the contents thereof shown in an exploded view.

As best seen in FIG. 5, the fourth packet 24 contains an instruction and chart booklet 74 and a number of sterile envelopes 76, each containing a number (e.g. 4) of thermometers 78. The instruction and chart booklet 74 contains information and instructions explaining the use of the charts 82 and thermometers 78 for keeping track of basal body temperature and for predicting ovulation. A sample chart 80 is included as an illustration of charting basal temperature. Each of the temperature charts 82, each being accompanied by a "recommendations" space 84, has a horizontal or X-axis corresponding to days, and containing spaces for noting the date, and has a vertical or Y-axis corresponding to temperatures, such as temperatures between 96.5° and 99.5° F., in increments of 0.1° F. The envelopes 76 constitute sterile containers for the thermometers 78. By providing sterile containers, the thermometers 78 can be maintained in a sterile condition until they are needed. In this way, the thermometers 78 can be used without rinsing or other unnecessary physical activity which might interfere with accurate measurement of basal temperature. The thermometers 78 are preferably single-use solid state thermometers. Such thermometers are available from Info-Chem, a subsidiary of PyMaH Corporation, and are identified by the trademarks Tempa-Dot Ready Strip TM.

Figure 6A:
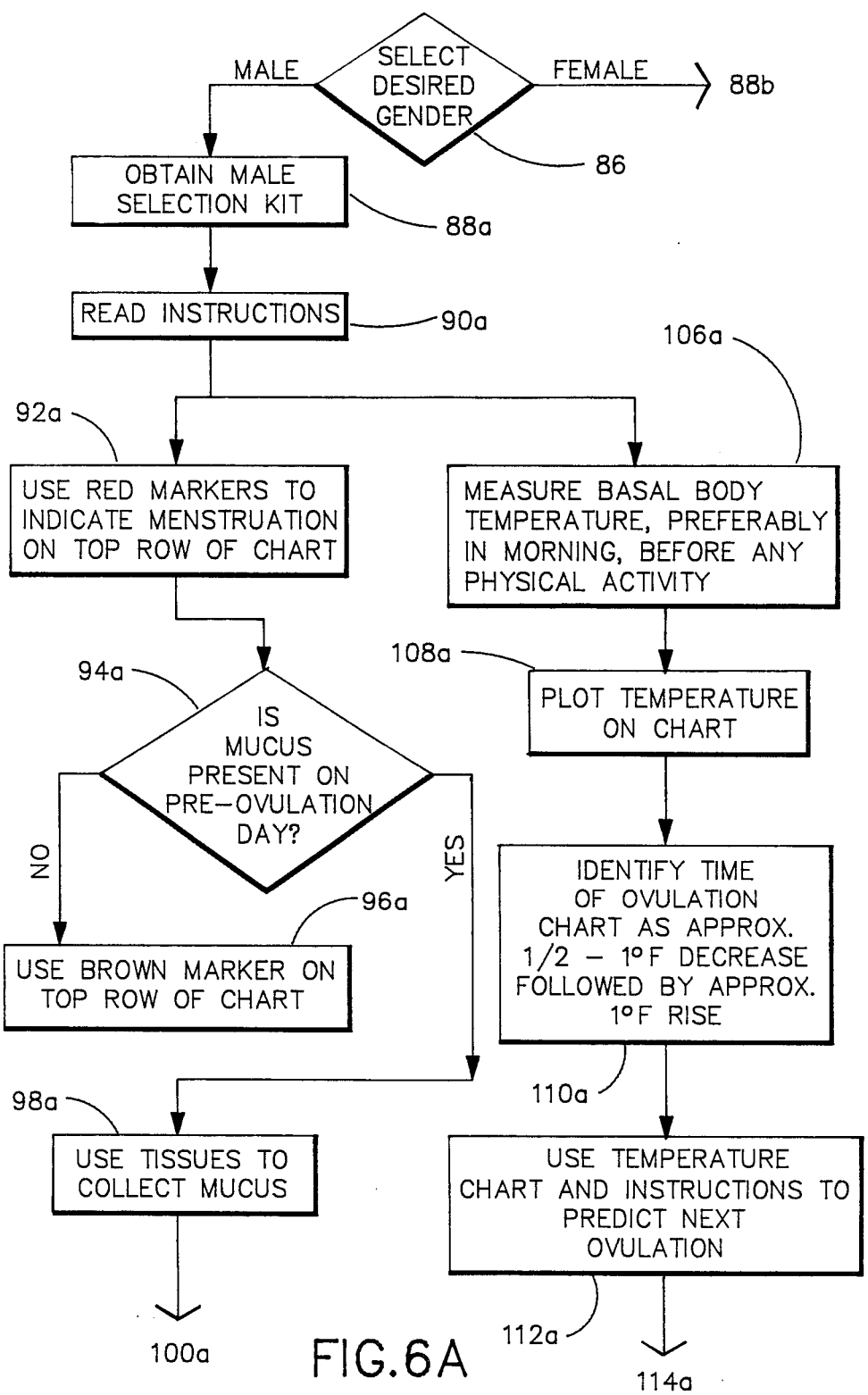
FIGS. 6A–6C are a flow diagram of the method of the present invention.
Figure 6B:
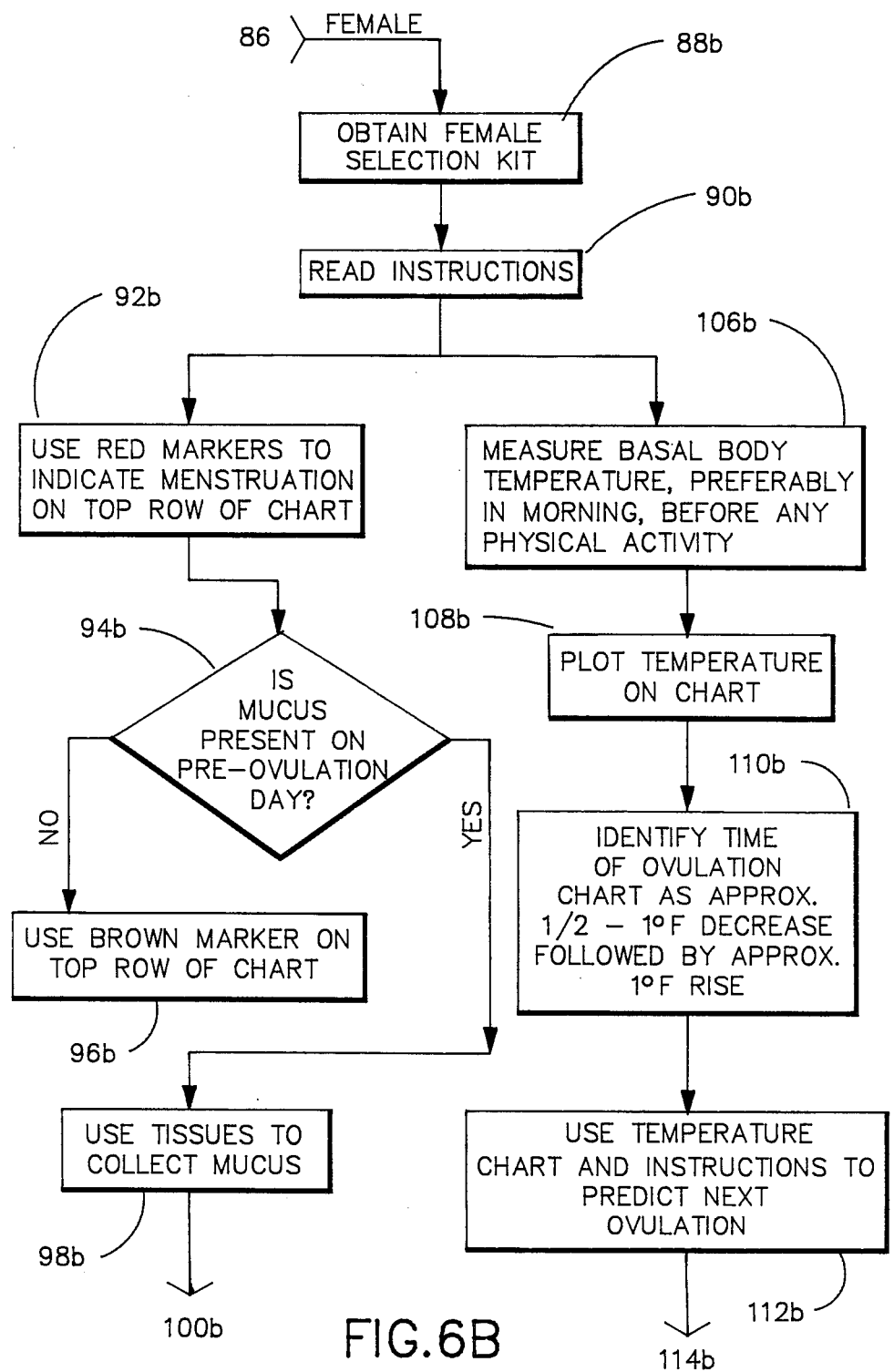
Figure 6E:
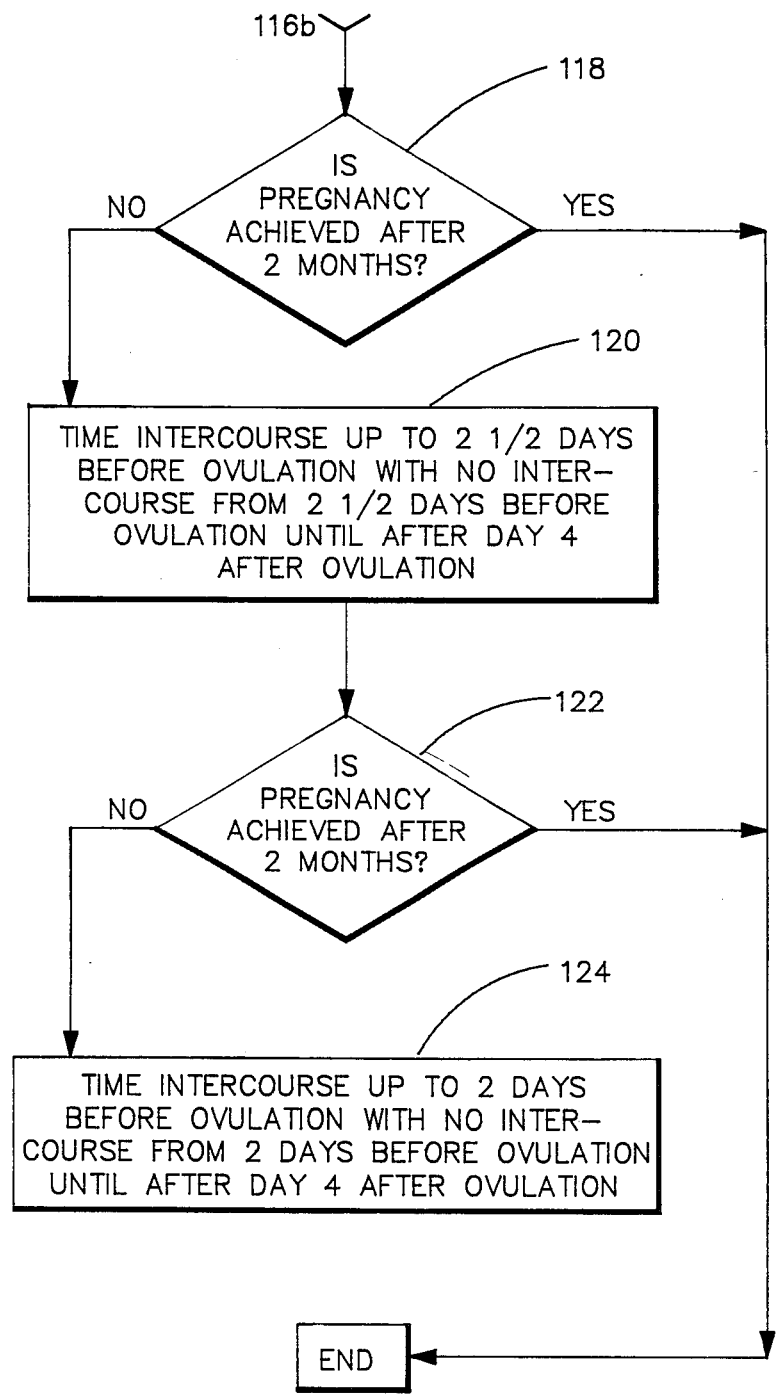

The method of attempting to conceive a child of a desired gender, and which involves the use of the kit will now be described. Referring to the steps illustrated in FIG. 6, after the gender desired for the child is selected 86, the appropriate kit is obtained 88a,b. The caddy 14 containing the packets 16–24 is removed from the box 12 and conveniently located. The instructions contained in the kit 10 are read 90a,b. The mucus method and the temperature method associated with ovulation predication are used, as described below, preferably through two or more menstrual cycles to form a basis for predicting and verifying the time of the next ovulation.

In accordance with the mucus method 92a,b–104a,b, the charts 68 and stickers 50–66 are used to monitor and record observations on the state of the mucus of the woman wishing to conceive a child. Preferably, instances of intercourse and whether intercourse occurs during the day or night are noted on the chart using the day and night indicia. Recording commences with the first day of menstruation. The date is entered into the chart on the spaces provided therefor. A red sticker 52 is placed on the top row of the chart during each day of menstruation 92a. Following menstruation, the woman checks each day for the presence of vaginal mucus 94a. If no mucus is present and ovulation has not yet occurred (as determined by the method described below) a brown sticker 56, 58 is placed on the top row of the chart 68 for the corresponding day 96a. If mucus is present, a tissue 70 from the third packet 22 is used to collect the mucus 98a. Using the instructions 36, the appearance and consistency of the mucus is compared to that depicted in the photograph stickers 50 of the first sheet 44. A sticker 50 most closely resembling the mucus is detached from the sheet 44 and placed in the corresponding space in the bottom row of the mucus chart 68, 100a. Using the instructions 36, a determination is made whether the condition of the mucus indicates that ovulation has occurred. Ovulation is considered to have occurred when the mucus is mostly clear, elastic and fluid. A marker for placement on the top row of the chart 68 is selected to correspond to the mucus sticker 50 which has been placed on the bottom row of the chart, taking into consideration whether ovulation has occurred 102a. If ovulation has not yet occurred, a white sticker bearing fertility indicia 62 is placed on the top row. On the day of ovulation, a peak indicia sticker 64 is placed on the top row. On days one through three after ovulation, a sticker bearing a fertility indicia is used. A yellow sticker bearing fertility indicia 66 is used on post-ovulation days when mucus is present. A brown sticker bearing fertility indicia 60 is used for post-ovulation days one through three when mucus is not present. On day four and subsequent days after ovulation, a yellow or brown sticker, without fertility indicia, is used. A yellow sticker 54 is used during days when mucus is present. A brown sticker 56, 58 is used during days when mucus is not present. A new chart 68 is started when menstruation begins.

Information on the mucus chart, plotted over two more menstrual cycles, is used to predict the day of next ovulation 104a,b. The usual or average number of days between ovulations is determined using the dates entered in the mucus chart. That number of days is counted forward from the date of last ovulation to determine the predicted date of next ovulation.

Simultaneously with using the mucus method to predict ovulation, the basal temperature method is also used to monitor ovulation and verify the prediction of the next ovulation date. That is, the temperature method for ovulation prediction is preferably used to verify or assure desired accuracy of the mucus technique for ovulation prediction. The temperature charts 82 are used to record basal body temperature on each day, using one chart for each cycle from the beginning of one menstrual period to the beginning of the next. The temperature is measured preferably immediately upon waking and preferably with a minimum of movement, before any substantial physical or mental activity occurs 106a. The measured temperature is recorded on the chart 82 for the corresponding day 108a. Using the instructions 36 and charts, the temperatures recorded are analyzed to determine on which day ovulation occurred 110a. Ovulation is indicated by a period in which basal temperature drops $\frac{1}{2}$ to 1 full degree in one day followed by a sharp rise in temperature, usually about a full degree, 24 hours after the initial drop in temperature. Following this rise, the temperature will normally remain high until the next menstrual period. The time of ovulation is considered to be the 24 hours following the drop in temperature. The instructions 36 and temperature charts 82 are used to predict the day of the next ovulation 112a,b. Two or more temperature charts are used to determine the average or normal number of days between ovulations using the dates written on the charts. This number of days is counted forward from the last day of ovulation to determine a predicted next day of ovulation. In this manner, the day of ovulation predicted using the temperature method is used to confirm the prediction made using the mucus method 114a,b.

The prediction of the next ovulation day and the instructions 34 are used to time intercourse with respect to the predicted day of ovulation 116a,b. When a male child is desired, intercourse is timed to occur on the day of ovulation, preferably within 12 hours after ovulation, with no intercourse on the days one through four prior to ovulation or days two or three after ovulation 116a. If conception is not achieved within a three to six month period, a physician should be consulted to determine if there are underlying fertility problems.

When conception of a female child is desired, the prediction of the day of ovulation and the instructions 36 are used to time intercourse from the end of the menstrual period through the fourth day prior to ovulation, i.e., up to the third day before ovulation with no intercourse during the period from the third day prior to ovulation until after the fourth day after ovulation 116b. If, after two months of attempting to conceive a female child using this method of timing intercourse it is determined that pregnancy has not been achieved 118, the period for intercourse is extended by $\frac{1}{2}$ day, i.e. intercourse is timed to occur in the period up to $2\frac{1}{2}$ days before ovulation, with no intercourse from day $2\frac{1}{2}$ before ovulation until day 4 after ovulation 120. If, after an additional two months on this second regime it is determined that pregnancy has not been achieved 122, the period for intercourse is extended another $\frac{1}{2}$ day, i.e. intercourse is timed to occur during the period up to 2 days before ovulation, with no intercourse from day 2 before ovulation until after day 4 after ovulation. If conception is not achieved within three to six months, a physician should be consulted to determine if there are underlying fertility problems.

The method of timing of intercourse with respect to ovulation is preferably combined with other methods to further improve the probability of conceiving a child of the desired gender. When it is desired to conceive a male, the husband should avoid sexual relations and the release of any seminal fluid from day three prior to ovulation until the day of ovulation. Couples trying to conceive a female child should have frequent intercourse during that time period determined in accordance with the recommended timing of intercourse for conceiving a female child.

When it is desired to conceive a male child, the man should enter the vagina from the rear and penetrate as deeply as possible during ejaculation. When it is desired to conceive a female child, the "missionary" position (woman lying on back, man on top) should be used and the man should practice shallow penetration at the time of ejaculation.

When it is desired to conceive a male child, the man should time his orgasm to follow that of the woman. When it is desired to conceive a female child, the woman should refrain from orgasm.

A number of advantages are obtained by using the disclosed kit and accompanying method. It has been observed that a child of the desired gender can be conceived using the present invention with a high degree of reliability (e.g. up to 85 percent reliability for conceiving a male child, up to 80 percent reliability for conceiving a female child). All information and apparatus needed for practicing this invention are provided in a single package or kit so that it is not necessary to go to a number of sources and purchase a variety of devices from different sources in order to practice this invention. The method for attempting to conceive a child of a desired gender is carried out in privacy. No complicated equipment or specialized skills is required. Not only does the kit and method include information and materials for use in predicting ovulation by the mucus method, the method also relies on a verification step relating to the monitoring of the basal body temperature of the woman.

The invention does not relate to a contraceptive method or device and should not be relied upon for contraceptive aid.

Although the present invention has been described with reference to a particular embodiment, it should be appreciated that modifications can be effected within the spirit and scope of the invention.

What is claimed is:

1. A method used in the home for use in attempting to conceive a child of a selected gender, comprising:
   accessing a single kit having a number of products, including:
      instructional literature means explaining the method including (a) means for providing information for use in predicting ovulation, (b) means for providing information relating to the placement of the sperm during intercourse wherein said information is directed to attempting to conceive a child of the selected gender, and (c) means for providing information associated with the timing of intercourse wherein said information is directed to attempting to conceive a child of the selected gender, and at least one of the following:
         mucus chart means for monitoring the state of the mucus of a woman attempting to conceive a child of the selected gender, and
         temperature means including temperature chart means and means for sensing body temperature for use in monitoring the body temperature of the woman;
   conducting at least one of the following two steps:
      monitoring the state of mucus of the woman by sight observation and using said mucus chart means, and
      keeping track of body temperature of the woman using said temperature chart means after obtaining the temperature of the body of the woman using said means for sensing body temperature; and
   attempting to conceive a child of the selected gender by having intercourse within a predetermined period of time relating to ovulation using at least one of information previously provided on said mucus chart means and information previously provided on said temperature chart means wherein, when attempting to conceive a female child, having intercourse days before ovulation and, when attempting to conceive a male child, having intercourse at about the time of ovulation, and by placing sperm during intercourse near the cervix of the woman when attempting to conceive a male child and placing sperm at shallow penetration when attempting to conceive a female child.

2. A method, as claimed in claim 1, wherein:
   said step of accessing said kit includes providing a kit having tissue means and said step of monitoring mucus includes using said tissue means to obtain the mucus.

3. A kit used in the home for use in providing information and in attempting to conceive a child of a selected gender, comprising:
   instructional literature means for providing information for use in attempting to conceive a child of the selected gender, including:
      means for providing information for use in predicting ovulation,
      means for providing information relating to the placement of the sperm during intercourse, and
      means for providing information associated with the timing of intercourse;
   chart means including at least one of the following:
      first chart means for monitoring the state of mucus of the woman desiring to conceive a child by sight observation, and
      second chart means for monitoring the temperature of the woman, said temperature of the woman being obtained using temperature sensing means;
   wherein said chart means is used to establish a desired time for engaging in intercourse to conceive a selected one of a female child and male child wherein intercourse is to occur days before ovulation when attempting to conceive a female child and intercourse is to occur at about the time of ovulation when attempting to conceive a male child and said instructional literature means is used to provide information concerning placement of the sperm and in which during intercourse the sperm is to be placed near the cervix of the woman when attempting to conceive a male child and the sperm is to be placed at shallow penetration when attempting to conceive a female child.

4. A kit, as claimed in claim 3, further including:
   tissue means for use in monitoring the state of the woman's mucus.

5. A kit, as claimed in claim 4 further including:
   an individual package for housing each of said instructional literature means, said temperature sensing means, and said tissue means, and a container for containing each of said individual packages, wherein said container includes a back wall having a greater height than a front wall and each of said packages is of a different size to permit ready viewing of indicia provided on each of said packages.

* * * * *